United States Patent
Von Novak, III et al.

(10) Patent No.: US 10,411,493 B2
(45) Date of Patent: Sep. 10, 2019

(54) PHASE AND MAGNITUDE CONTROL FOR WIRELESS POWER TRANSMITTERS

(71) Applicant: QUALCOMM Incorporated, San Diego, CA (US)

(72) Inventors: William Henry Von Novak, III, San Diego, CA (US); Mark White, II, San Diego, CA (US); Seong Heon Jeong, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 45 days.

(21) Appl. No.: 15/597,944

(22) Filed: May 17, 2017

(65) Prior Publication Data
US 2018/0337546 A1   Nov. 22, 2018

(51) Int. Cl.
*H02J 7/00* (2006.01)
*H02J 7/02* (2016.01)
*A61N 1/378* (2006.01)
*H02J 50/12* (2016.01)
*H01F 38/14* (2006.01)
*H02J 50/80* (2016.01)

(52) U.S. Cl.
CPC ............ *H02J 7/025* (2013.01); *A61N 1/3787* (2013.01); *H02J 50/12* (2016.02); *H01F 38/14* (2013.01); *H02J 50/80* (2016.02); *H02J 2007/0096* (2013.01)

(58) Field of Classification Search
CPC ...................................................... H02J 7/025
USPC ........................................................ 320/108
See application file for complete search history.

(56) References Cited

U.S. PATENT DOCUMENTS

| | | | |
|---|---|---|---|
| 8,886,333 B2* | 11/2014 | Lui | A61N 1/3787 607/61 |
| 9,192,772 B1* | 11/2015 | Tsukamoto | A61N 1/3605 |
| 9,929,584 B2* | 3/2018 | Aghassian | H02J 7/025 |
| 2003/0191504 A1* | 10/2003 | Meadows | A61N 1/36071 607/33 |
| 2013/0300205 A1 | 11/2013 | Tzanidis et al. | |
| 2014/0091756 A1* | 4/2014 | Ofstein | H02J 5/005 320/108 |
| 2016/0013661 A1 | 1/2016 | Kurs et al. | |
| 2016/0087458 A1* | 3/2016 | Grbic | H02J 5/005 307/104 |
| 2016/0087477 A1 | 3/2016 | Jeong et al. | |

(Continued)

*Primary Examiner* — Suchin Parihar
(74) *Attorney, Agent, or Firm* — Patterson & Sheridan, LLP

(57) ABSTRACT

Certain aspects of the present disclosure are generally directed to apparatus and techniques for wireless charging. One example apparatus generally includes a plurality of inductive elements and signal generation circuitry coupled to the plurality of inductive elements and configured to generate a plurality of signals, where at least two signals of the plurality of signals have different magnitudes. In certain aspects, the signal generation circuitry is configured to drive the plurality of inductive elements using the plurality of signals, where at least one first inductive element of the plurality of inductive elements is driven using at least one first signal of the plurality of signals having a first phase and at least one second inductive element of the plurality of inductive elements is driven using at least one second signal of the plurality of signals having a second phase different from the first phase.

27 Claims, 7 Drawing Sheets

(56) References Cited

U.S. PATENT DOCUMENTS

| | | | |
|---|---|---|---|
| 2016/0126771 A1* | 5/2016 | Aghassian | H02J 7/025 |
| | | | 320/108 |
| 2016/0220394 A1* | 8/2016 | Griffith | A61B 5/0031 |
| 2016/0226292 A1 | 8/2016 | Yoon | |
| 2016/0241075 A1 | 8/2016 | Von, III et al. | |
| 2016/0294225 A1* | 10/2016 | Blum | H02J 5/005 |
| 2017/0005527 A1 | 1/2017 | Ishihara | |
| 2017/0201118 A1* | 7/2017 | Nejatali | H02J 7/025 |

\* cited by examiner

500 ⟶

| Magnitude and Phase | A | B | C | D |
|---|---|---|---|---|
| 1 | 1 x 0° | 1 x 0° | 1 x 0° | 1 x 0° |
| 2 | 1 x 40° | 1.3 x 40° | 1.3 x 40° | 1 x 40° |
| 3 | 1 x 80° | 1.3 x 80° | 1.3 x 80° | 1 x 80° |
| 4 | 1 x 120° | 1 x 120° | 1 x 120° | 1 x 120° |

| Size of RCVR | Linear | Linear with Phase Adjustment | Square | Square with Phase Adjustment |
|---|---|---|---|---|
| 1 | 10V | 10V | 10V | 10V |
| 2 | 20V | 18.8V | 40V | 37.6V |
| 3 | 30V | 25.3V | 90V | 75.9V |
| 4 | 40V | 28.8V | 160V | 115V |

FIG. 6

PHASE AND MAGNITUDE CONTROL FOR WIRELESS POWER TRANSMITTERS

TECHNICAL FIELD

The present disclosure relates generally to electronic devices, and in particular, to wireless charging.

BACKGROUND

An increasing number and variety of electronic devices are powered via rechargeable batteries. Such devices include mobile phones, portable music players, laptop computers, tablet computers, computer peripheral devices, communication devices (e.g., Bluetooth devices), digital cameras, hearing aids, medical implants, and the like. While battery technology has improved, battery-powered electronic devices increasingly demand and consume greater amounts of power. As such, these devices constantly require recharging. Rechargeable devices are often charged via wired connections that employ cables or other similar connectors that are physically connected to a power supply. Cables and similar connectors may sometimes be inconvenient or cumbersome and have other drawbacks. Wireless power transfer systems, for example, may allow users to charge and/or power electronic devices without physical, electrical connections, thus reducing the number of components involved for operation of the electronic devices and simplifying the use thereof.

For example, some battery-powered devices, such as medical implants (e.g., pacemakers, neuromodulation devices, insulin pumps, etc.) may be located in areas where replacing the battery is not always feasible (e.g., in a body, such as a human body). For example, to change a battery for a medical implant, surgery may need to be performed, which is risky. Accordingly, it may be safer to charge such devices wirelessly.

Further, some electronic devices may not be battery powered, but it still may be beneficial to use wireless power transfer to power such devices. In particular, the use of wireless power may eliminate the need for cords or cables to be attached to the electronic devices, which may be inconvenient and aesthetically displeasing.

Different electronic devices may have different shapes, sizes, and power specifications. There is flexibility in having different sizes and shapes in the components (e.g., magnetic coil, charging plate, etc.) that make up a wireless power transmitter and/or a wireless power receiver in terms of industrial design and support for a wide range of devices.

SUMMARY

Certain aspects of the present disclosure are directed to an apparatus for wireless charging. The apparatus generally includes a plurality of inductive elements and signal generation circuitry coupled to the plurality of inductive elements, the signal generation circuitry being configured to generate a plurality of signals, at least two signals of the plurality of signals having different magnitudes. In certain aspects, the signal generation circuitry is configured to drive the plurality of inductive elements using the plurality of signals, at least one first inductive element of the plurality of inductive elements being driven using at least one first signal of the plurality of signals having a first phase and at least one second inductive element of the plurality of inductive elements being driven using at least one second signal of the plurality of signals having a second phase different from the first phase Certain aspects of the present disclosure are directed to an apparatus for wireless charging. The apparatus generally includes a plurality of inductive elements, a controller configured to receive an indication of whether a power receiving unit (PRU) is receiving sufficient charge and generate at least one control signal based on the indication, and signal generation circuitry coupled to the plurality of inductive elements and configured to generate a plurality of signals based on the control signal, at least one phase of the plurality of signals being set by the control signal based on the indication, and drive the plurality of inductive elements using the plurality of signals.

Certain aspects of the present disclosure are directed to a method for wireless charging. The method generally includes generating a plurality of signals, at least two signals of the plurality of signals having different magnitudes, and driving a plurality of inductive elements using the plurality of signals, at least one first inductive element of the plurality of inductive elements being driven using at least one first signal of the plurality of signals having a first phase and at least one second inductive element of the plurality of inductive elements being driven using at least one second signal of the plurality of signals having a second phase different from the first phase.

Certain aspects of the present disclosure are directed to a method for wireless charging. The method generally includes receiving an indication of whether a PRU is receiving sufficient charge, generating at least one control signal based on the indication, generating a plurality of signals based on the control signal, at least one phase of the plurality of signals being set by the control signal based on the indication, and driving a plurality of inductive elements using the plurality of signals.

Other aspects, features, and embodiments of the present disclosure will become apparent to those of ordinary skill in the art, upon reviewing the following description of specific, exemplary aspects of the present disclosure in conjunction with the accompanying figures. While features of the present disclosure may be discussed relative to certain aspects and figures below, all aspects of the present disclosure can include one or more of the advantageous features discussed herein. In other words, while one or more aspects may be discussed as having certain advantageous features, one or more of such features may also be used in accordance with the various aspects of the present disclosure. In similar fashion, while exemplary aspects may be discussed below as device, system, or method aspects it should be understood that such exemplary aspects can be implemented in various devices, systems, and methods.

The following detailed description and accompanying drawings provide a better understanding of the nature and advantages of the present disclosure.

BRIEF DESCRIPTION OF THE DRAWINGS

With respect to the discussion to follow and in particular to the drawings, it is stressed that the particulars shown represent examples for purposes of illustrative discussion, and are presented in the cause of providing a description of principles and conceptual aspects of the present disclosure. In this regard, no attempt is made to show implementation details beyond what is needed for a fundamental understanding of the present disclosure. The discussion to follow, in conjunction with the drawings, makes apparent to those of skill in the art how embodiments in accordance with the present disclosure may be practiced. In the accompanying drawings:

FIG. 5 is a table illustrating magnitude and phase of signals applied to the coils of FIG. 4, in accordance with certain aspects of the present disclosure.

FIG. 6 is a table illustrating the voltage coupled onto a receive coil with and without phase adjustment, in accordance with certain aspects of the present disclosure.

DETAILED DESCRIPTION

Figure 1:
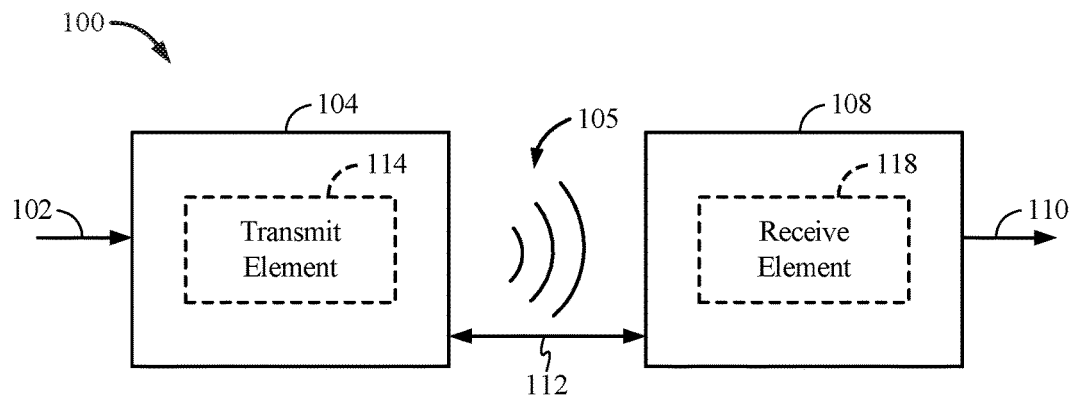
FIG. 1 is a functional block diagram of an example wireless power transfer system, in accordance with certain aspects of the present disclosure.

Drawing elements that are common among the following figures may be identified using the same reference numerals.

Wireless power transfer may refer to transferring any form of energy associated with electric fields, magnetic fields, electromagnetic fields, or otherwise from a transmitter to a receiver without the use of physical electrical conductors (e.g., power may be transferred through free space or air). The power output into a wireless field (e.g., a magnetic field or an electromagnetic field) may be received, captured by, or coupled by a "wireless power receiving element" to achieve power transfer.

Example Wireless Power Transfer Systems

FIG. 1 is a functional block diagram of an example wireless power transfer system 100, in accordance with certain aspects of the present disclosure. Input power 102 may be provided to a transmitter 104 (also referred to as a power transfer unit or power transmitting unit (PTU)) from a power source (not shown in this figure) to generate a wireless (e.g., magnetic or electromagnetic) field 105 for performing energy transfer. A receiver 108 (also referred to as a power receiving unit (PRU)) may be introduced into the wireless field 105 and generate output power 110 for storing or consumption by a device (not shown in this figure) coupled to the output power 110. The transmitter 104 and the receiver 108 may be separated by a distance 112. The transmitter 104 may include a wireless power transmitting element 114 for transmitting/coupling energy to the receiver 108. The receiver 108 may include a wireless power receiving element 118 for receiving or capturing energy transmitted from the transmitter 104.

In one illustrative aspect, the transmitter 104 and the receiver 108 may be configured according to a mutual resonant relationship. When the resonant frequency of the receiver 108 and the resonant frequency of the transmitter 104 are substantially the same or very close, transmission losses between the transmitter 104 and the receiver 108 are reduced. As such, wireless power transfer may be provided over larger distances. Resonant inductive coupling techniques may thus allow for improved efficiency and power transfer over various distances and with a variety of inductive power transmitting and receiving element configurations.

In certain aspects, the wireless field 105 may correspond to the "near field" of the transmitter 104. The near field may correspond to a region in which there are strong reactive fields resulting from the currents and charges in the power transmitting element 114 that minimally radiate power away from the power transmitting element 114. The near field may correspond to a region that is within about one wavelength (or a fraction thereof) of the power transmitting element 114. Conversely, the far field may correspond to a region that is greater than about one wavelength of the power transmitting element 114.

In certain aspects, efficient energy transfer may occur by coupling a large portion of the energy in the wireless field 105 to the power receiving element 118, rather than propagating most of the energy in an electromagnetic wave to the far field.

In certain implementations, the transmitter 104 may output a time-varying magnetic (or electromagnetic) field with a frequency corresponding to the resonant frequency of the wireless power transmitting element 114. When the receiver 108 is within the wireless field 105, the time varying magnetic (or electromagnetic) field may induce a current in the wireless power receiving element 118. As described above, if the wireless power receiving element 118 is configured as a resonant circuit to resonate at the frequency of the wireless power transmitting element 114, energy may be efficiently transferred. An alternating current (AC) signal induced in the wireless power receiving element 118 may be rectified to produce a direct current (DC) signal that may be provided to charge or to power a load.

Figure 2:
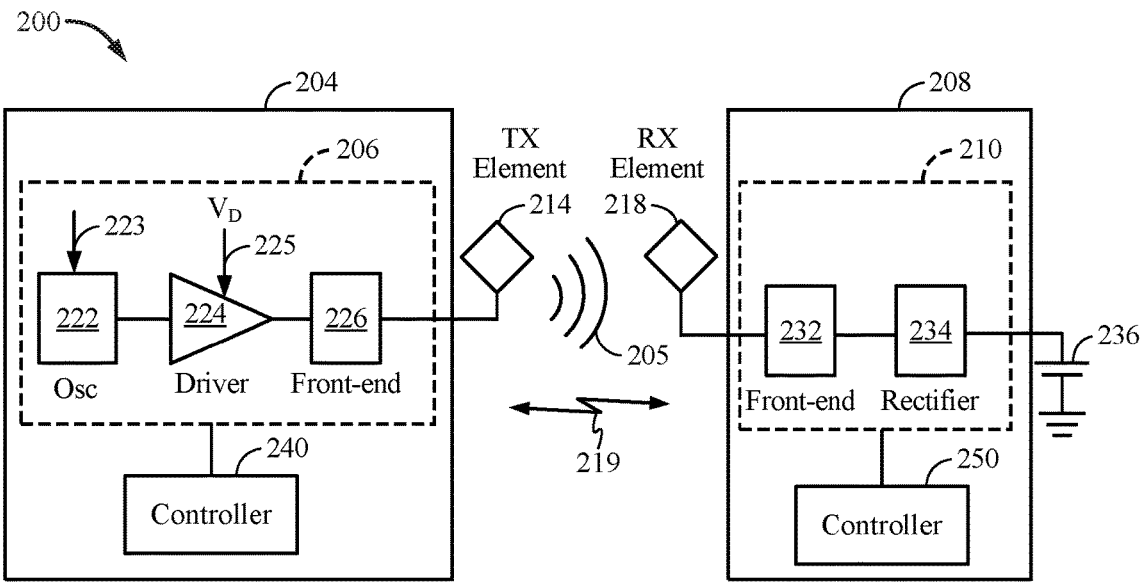
FIG. 2 is a more-detailed block diagram of an example wireless power transfer system, in accordance with certain aspects of the present disclosure.

FIG. 2 is a more-detailed block diagram of an example wireless power transfer system 200, in accordance with certain aspects of the present disclosure. The system 200 may include a transmitter 204 and a receiver 208. The transmitter 204 may include transmit circuitry 206 that may include an oscillator 222, a driver circuit 224, and a front-end circuit 226. The oscillator 222 may be configured to generate an oscillator signal at a desired frequency and phase, which may be adjusted in response to a frequency control signal 223. The oscillator 222 may provide the oscillator signal to the driver circuit 224. The driver circuit 224 may be configured to drive the power transmitting element 214 at, for example, a resonant frequency of the power transmitting element 214 based on an input voltage signal ($V_D$) 225. The driver circuit 224 may be a switching amplifier configured to receive a square wave from the oscillator 222 and output a sine wave.

The front-end circuit 226 may include a filter circuit configured to filter out harmonics or other unwanted frequencies. The front-end circuit 226 may include a matching circuit configured to match the impedance of the transmitter 204 to the impedance of the power transmitting element 214. As explained in more detail below, the front-end circuit 226 may include a tuning circuit to create a resonant circuit with the power transmitting element 214. As a result of driving the power transmitting (TX) element 214, the TX element 214 may generate a wireless field 205 to wirelessly output power at a level sufficient for charging a battery 236, or otherwise powering a load.

The transmitter 204 may further include a controller 240 operably coupled to the transmit circuitry 206 and configured to control one or more aspects of the transmit circuitry 206, or accomplish other operations relevant to managing the transfer of power. For example, the controller 240 may generate a control signal for controlling at least one of a phase or magnitude of signal used to drive the TX element 214. The controller 240 may be a micro-controller or a processor. The controller 240 may be implemented as an application-specific integrated circuit (ASIC). The controller 240 may be operably connected, directly or indirectly, to each component of the transmit circuitry 206. The controller 240 may be further configured to receive information from each of the components of the transmit circuitry 206 and perform calculations based on the received information. The controller 240 may be configured to generate control signals (e.g., signal 223) for each of the components that may adjust the operation of that component. As such, the controller 240 may be configured to adjust or manage the power transfer based on a result of the operations performed by it. In some cases, the transmitter 204 may further include a memory (not shown) configured to store data, for example, such as instructions for causing the controller 240 to perform particular functions, such as those related to management of wireless power transfer as described in more detail herein.

Certain aspects of the present disclosure provide signal generation circuitry, which may include one or more transmitters (e.g., transmitter 206) for driving one or more inductive elements (e.g., power transmitting element 214). For example, the signal generation circuitry may include one or more oscillators (e.g., oscillator 222), one or more driver circuits (e.g., driver circuit 225) and one or more front-end circuits (e.g., front-end circuit 226) to generate signals for transmission via the inductive elements. In certain aspects, the signal generation circuitry may be configured to independently control the phase and magnitude of the signals to be transmitted via the inductive elements based on one or more control signals received from a controller (e.g., controller 240).

The receiver 208 may include receive circuitry 210 that may include a front-end circuit 232 and a rectifier circuit 234. The front-end circuit 232 may include matching circuitry configured to match the impedance of the receive circuitry 210 to the impedance of the power receiving element 218. The transmitting and receiving elements 214 and 218 may also be referred to herein as wireless charging elements. As explained below, the front-end circuit 232 may further include a tuning circuit to create a resonant circuit with the power receiving element 218. The rectifier circuit 234 may generate a DC power output from an AC power input to charge the battery 236, as shown in FIG. 2. The receiver 208 and the transmitter 204 may additionally communicate on a separate communication channel 219 (e.g., Bluetooth, Zigbee, cellular, etc.). The receiver 208 and the transmitter 204 may alternatively communicate via in-band signaling using characteristics of the wireless field 205.

In certain aspects of the present disclosure, the receiver 208 may be configured to determine whether an amount of power transmitted by the transmitter 204 and received by the receiver 208 is appropriate for charging the battery 236. In certain aspects, the transmitter 204 may be configured to generate a predominantly non-radiative field with a direct field coupling coefficient (k) for providing energy transfer.

Receiver 208 may directly couple to the wireless field 205 and may generate an output power for storing or consumption by a battery (or load) 236 coupled to the output or receive circuitry 210.

The receiver 208 may further include a controller 250 configured similarly to the transmit controller 240 as described above for managing one or more aspects of the wireless power receiver 208. The receiver 208 may further include a memory (not shown) configured to store data, such as instructions for causing the controller 250 to perform particular functions, such as those related to management of wireless power transfer. As discussed above, transmitter 204 and receiver 208 may be separated by a distance and may be configured according to a mutual resonant relationship to reduce transmission losses between the transmitter 204 and the receiver 208.

Figure 3:
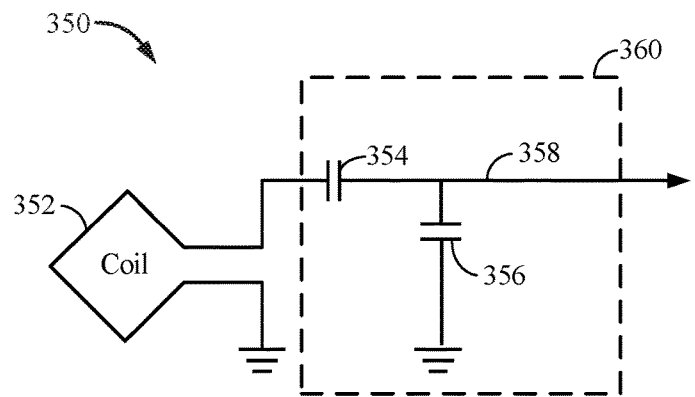
FIG. 3 is a schematic diagram of a portion of example transmit circuitry or receive circuitry of FIG. 2 including a power transmitting or receiving element, in accordance with certain aspects of the present disclosure.

FIG. 3 is a schematic diagram of a portion of the transmit circuitry 206 or the receive circuitry 210 of FIG. 2, in accordance with certain aspects of the present disclosure. As illustrated in FIG. 3, transmit or receive circuitry 350 may include a power transmitting or receiving element 352 and a tuning circuit 360. The power transmitting or receiving element 352 may also be referred to or be configured as an antenna or a "loop" antenna. The term "antenna" generally refers to a component that may wirelessly output or receive energy for coupling to another antenna. The power transmitting or receiving element 352 may also be referred to herein or be configured as a "magnetic" antenna, or an induction coil, a resonator, or a portion of a resonator. The power transmitting or receiving element 352 may also be referred to as a coil or resonator of a type that is configured to wirelessly output or receive power. As used herein, the power transmitting or receiving element 352 is an example of a "power transfer component" of a type that is configured to wirelessly output and/or receive power. The power transmitting or receiving element 352 may include an air core or a physical core such as a ferrite core (not shown in this figure).

When the power transmitting or receiving element 352 is configured as a resonant circuit or resonator with tuning circuit 360, the resonant frequency of the power transmitting or receiving element 352 may be based on inductance and capacitance. Inductance may be simply the inductance created by a coil and/or other inductor forming the power transmitting or receiving element 352. Capacitance (e.g., a capacitor) may be provided by the tuning circuit 360 to create a resonant structure at a desired resonant frequency. As a non-limiting example, the tuning circuit 360 may comprise a capacitor 354 and a capacitor 356, which may be added to the transmit and/or receive circuitry 350 to create a resonant circuit.

The tuning circuit 360 may include other components to form a resonant circuit with the power transmitting or receiving element 352. As another non-limiting example, the tuning circuit 360 may include a capacitor (not shown) placed in parallel between the two terminals of the circuitry 350. Still other designs are possible. In some aspects, the tuning circuit in the front-end circuit 226 may have the same design as the tuning circuit in front-end circuit 232. In other aspects, the front-end circuit 226 may use a tuning circuit design different than in the front-end circuit 232.

For power transmitting elements, the signal 358, with a frequency that substantially corresponds to the resonant frequency of the power transmitting or receiving element 352, may be an input to the power transmitting or receiving element 352. For power receiving elements, the signal 358, with a frequency that substantially corresponds to the resonant frequency of the power transmitting or receiving element 352, may be an output from the power transmitting or receiving element 352. Although aspects disclosed herein may be generally directed to resonant wireless power transfer, persons of ordinary skill will appreciate that aspects disclosed herein may be used in non-resonant implementations for wireless power transfer.

Phase and Magnitude Control for Wireless Power Transmitters

In certain aspects, the transmitter 204 may be configured to transfer power to devices of different sizes. For example, wireless charging of small and large devices is currently supported by several standards. Therefore, it is important to design a wireless charging system that supports a wide range of device powers, sizes, and positions.

The voltage induced in a receive coil, such as the power receiving (RX) element 218 of FIG. 2, by magnetic fields from a transmitter is proportional to the square of the diameter of the receive coil, and the power induced in the receive coil is proportional to the cube of the diameter. This means that small devices may have trouble receiving enough power for efficient operation because they may have a smaller receive coil. On the other hand, larger devices having larger coils may have the opposite problem. For example, the voltage induced in the receive coil of larger devices may be too high. While it may not be difficult to make the coil within a larger device smaller, it is often difficult to make the coil in a small device larger. Certain aspects of the present disclosure provide techniques for attenuating a magnetic field as seen by larger devices with little to no effect on the magnetic field as seen by smaller devices. Certain aspects of the present disclosure also increase uniformity of the magnetic field generated by a transmitter (e.g., transmitter 204), which assists with efficient power transfer to a receiver (e.g., receiver 208).

Figure 4:
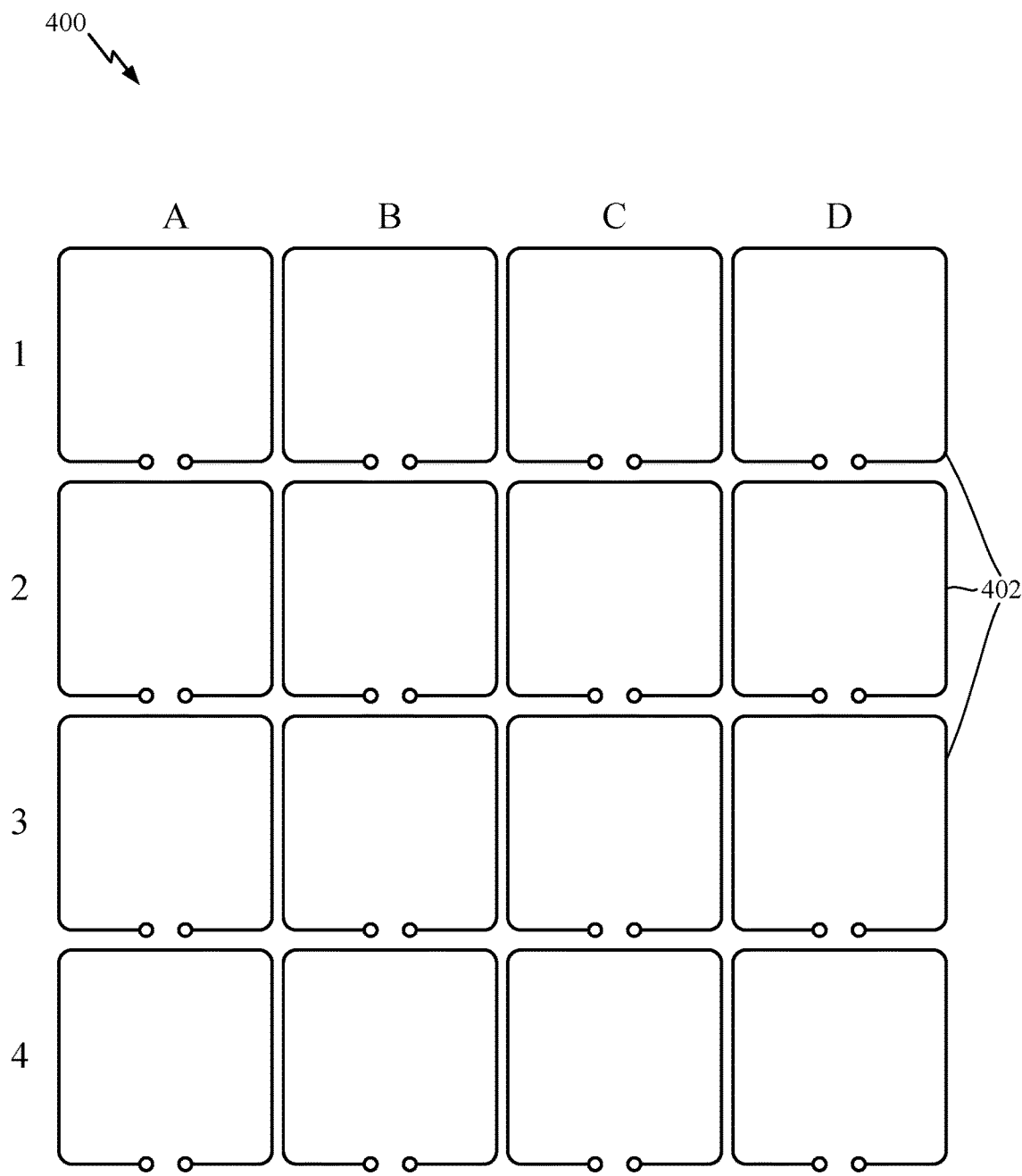
FIG. 4 illustrates an example arrangement of coils, in accordance with certain aspects of the present disclosure.

FIG. 4 illustrates an arrangement 400 of coils 402, in accordance with certain aspects of the present disclosure. For example, the TX element 214 may be implemented using multiple coils 402 in accordance with the arrangement 400 shown in FIG. 4. Each of the coils 402 may be coupled to separate transmit circuitry, such as the transmit circuitry 206, allowing for independent control of the magnitude and phase of signals applied to each of the coils 402.

If a wireless charging pad is made of several small coils as illustrated in FIG. 4, the magnetic fields generated by the coils sum together to create one larger field if the signals applied to all the coils are in phase. The magnitude of current in each loop will determine the field in that location. However, due to cancellation of counter-direction currents, a large array of smaller loops tends to have a magnetic field concentration towards the edges of the coil arrangement, resulting in a magnetic field that is not uniform. Certain aspects of the present disclosure maintain a uniform magnetic field by increasing the magnitude of the current in the center coils (or at least the coils relatively closer to the center of the arrangement).

In addition, aspects of the present disclosure support charging of small and large devices by controlling a phase of signals used to drive each of the coils. For example, if two transmit coils are side by side, and one receive coil is large enough to be disposed adjacent to both the transmit coils, then the net field received by the receive coil will be:

$$H \times \cos(\Phi)$$

where $\Phi$ is the difference in phase between the signals used to drive the two coils. Thus, a monotonically increasing phase from one coil to the next may have little to no effect on small devices having a small receive coil, but may attenuate the magnetic field as seen by larger devices having a large receive coil. Moreover, a monotonically increasing phase from one coil to the next may reduce the overall energy absorbed by more distant objects (e.g., a human being) since the fields tend to cancel far from the charging pad or other power transmitting element.

FIG. 5 is a table 500 illustrating example magnitudes and phases of signals applied to the coils 402, in accordance with certain aspects of the present disclosure. The table 500 provides the magnitude and phase for each of sixteen coils arranged in accordance with the arrangement 400 shown in FIG. 4. As presented above, it is desirable for a wireless power system to provide an even field for charging of devices on the charging pad. As illustrated by table 500, most of the coils 402 may be provided a current signal with a magnitude of one ampere (A) to create the charging fields. In order to make the magnetic field generated by the coils 402 more uniform, coils located in the center portion of the arrangement (coils B2, B3, C2, and C3) are driven with a larger current magnitude (e.g., 1.3 A) to counteract the lower magnetic field concentration in the center of the coil arrangement caused by field cancellation of adjacent conductors. In addition, the phases of the current signals applied to the coils 402 are adjusted gradually from a reference of 0° to 120° from row one to row four of the arrangement 400 to attenuate the magnetic field as seen by large receiver devices.

FIG. 6 is a table 600 illustrating the voltage coupled onto a receive coil with and without phase adjustment, in accordance with certain aspects of the present disclosure. The table 600 shows voltages as seen by a receiver for a linear arrangement of transmit coils and a square arrangement of transmit coils. The coil size of the linear arrangement design expands incrementally in one direction. For example, size one of the linear arrangement corresponds to one transmit coil in the arrangement and size four corresponds to four transmit coils in the arrangement. The coil size of the square arrangement design increases geometrically. For example, size one of the square arrangement corresponds to one transmit coil, size two corresponds to four transmit coils, size three corresponds to nine transmit coils, and size four corresponds to sixteen transmit coils.

As illustrated in table 600, for the linear arrangement with all coils receiving the same phase, the voltage seen by a receive coil increases linearly, proportional to the coil arrangement size. Therefore, without phase adjustment, the voltage range as seen by the receive coil is 4:1, making the receiver design difficult. However, by using phase adjustment, the voltage range is reduced to 2.9:1 which is easier to design for than 4:1. For the square arrangement with all coils receiving the same phase, the voltage seen by a receive coil increases geometrically, proportional to the size. Therefore, without phase adjustment, the voltage range is 16:1. With phase adjustment for the square arrangement, however, the voltage range is 11.5:1. Moreover, when using phase adjustment, the voltage magnitudes shown in table 500 can be calculated through simple vector addition.

If the voltage as seen by a receiver is too high, the phase difference between transmit coils (e.g., row to row) as described with respect to FIG. 4 can be increased. Likewise, if more power is desired (which generally means more voltage) then the phase difference between the transmit coils can be decreased.

The effect on voltage (and power) using phase adjustment is independent from compensation that can be implemented by changing the magnitude of signals used to drive the transmit coils. For example, phase adjustment can be used to compensate for larger devices, and the magnitude of signals used to drive each transmit coil can be controlled to generate a uniform magnetic field or to adjust the field to compensate for large metal (or large ferrite) masses on the charging pad, which can distort the field.

In certain aspects, only the coils that are in charging proximity to a receiver may be activated to reduce power consumption and address exposure issues. For example, in some cases, all the coils may be deactivated and periodically activated to detect whether a receiver is in proximity for charging via one or more of the coils. If a receiver is detected, the coils that are in proximity to the receiver may be activated for charging.

Multi-coil Field Steering

Certain aspects of the present disclosure are generally directed to eliminating, or at least reducing, dead spots in magnetic fields used to provide charge to a receiver. This is especially important when the receiver is an implantable device. Medical "neuromodulation" implants are becoming more popular. These are small devices that attach to nerves on animals and allow both monitoring and stimulation of nerves. This allows for efficient diagnosis and treatment of some diseases. Several other medical implants such as insulin level monitors, insulin pumps, and pacemakers are also becoming more popular. All these devices use electric power to operate. This power generally comes from a battery that may be rechargeable. For example, in some cases, it may be dangerous and risky to have primary batteries in these implants that may be replaced periodically by surgery. Therefore, it would be safer to use rechargeable batteries than can be charged wirelessly. Communication between each implant receiver and the power transmitter may be used to ensure that the receiver is charging at an appropriate voltage level.

Designing a transmitter and receiver implant which have good coupling regardless of implant depth or orientation is important and challenging. For example, some transmitter designs may result in dead spots or areas where a certain receiver orientation leads to near zero coupling. Certain aspects of the present disclosure allow for greater versatility to adjust the H-field direction so as to avoid these dead spots.

Figure 7:
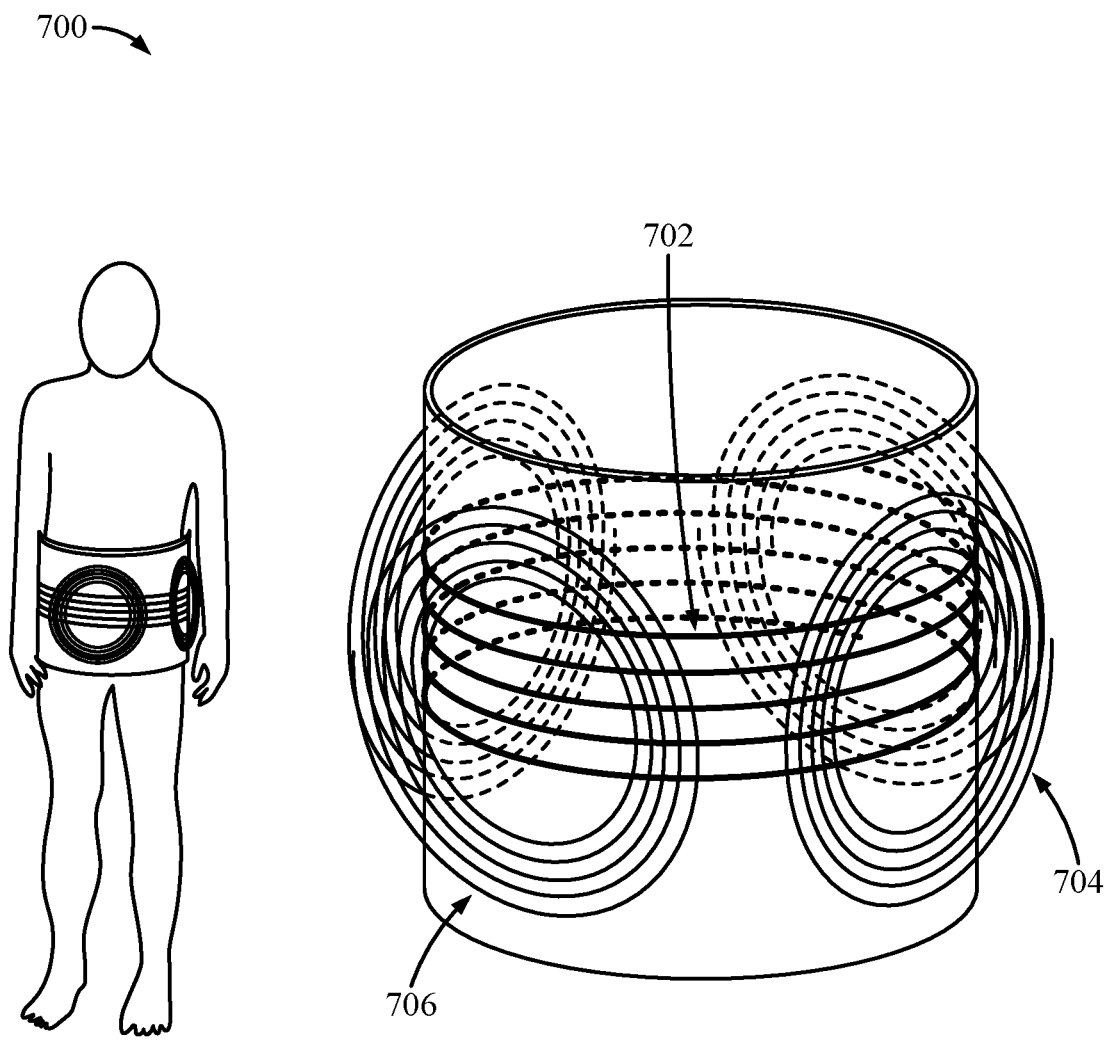
FIG. 7 illustrates a wearable transmitter antenna system implemented with different types of coils, in accordance with certain aspects of the disclosure.

FIG. 7 illustrates an example wearable transmitter antenna system 700 implemented with different types of coils, in accordance with certain aspects of the disclosure. For example, the transmitter antenna system 700 may include a circumferential coil 702 which creates vertical H-fields, a left-to-right Helmholtz coil 704, which creates a horizontal H-field from left to right, and a front-to-back Helmholtz coil 706 which creates a horizontal H-field from front to back. Each Helmholtz coil includes two circular magnetic coils positioned on the same axis to produce a region with a nearly uniform magnetic field. By switching between these three sets of coils, the H-field generated can accommodate various orientations of the receiver implant. However, the magnetic field generated by the transmitter antenna system 700 may have dead spots or areas with weak magnetic coupling to a receiver.

If an implant were to exist in or near a dead spot, this scenario could result in a patient being unable to charge his implant. In certain aspects of the present disclosure, one or more of the coils of the transmitter antenna system 700 may be driven with signals having different phases to eliminate, or at least reduce, dead spots by adjusting the H-field direction.

In certain aspects, a transmitter may be coupled to multiple coils having an arrangement 400 as described with respect to FIG. 4. The coils 402 may be driven with different phases to mitigate dead spots and poor coupling orientations between an implant and a transmitter. For example, the coils 402 may be driven with signals having different phases to control the flow of the magnetic fields generated by the coils and eliminate, or at least reduce, dead spots. In some cases, one or more coils may be driven with signals having a 180° phase offset as compared to signals used to drive one or more other coils in order to facilitate the H-field to flow from the in-phase coil(s) towards the out-of-phase coil(s).

Figure 8A:
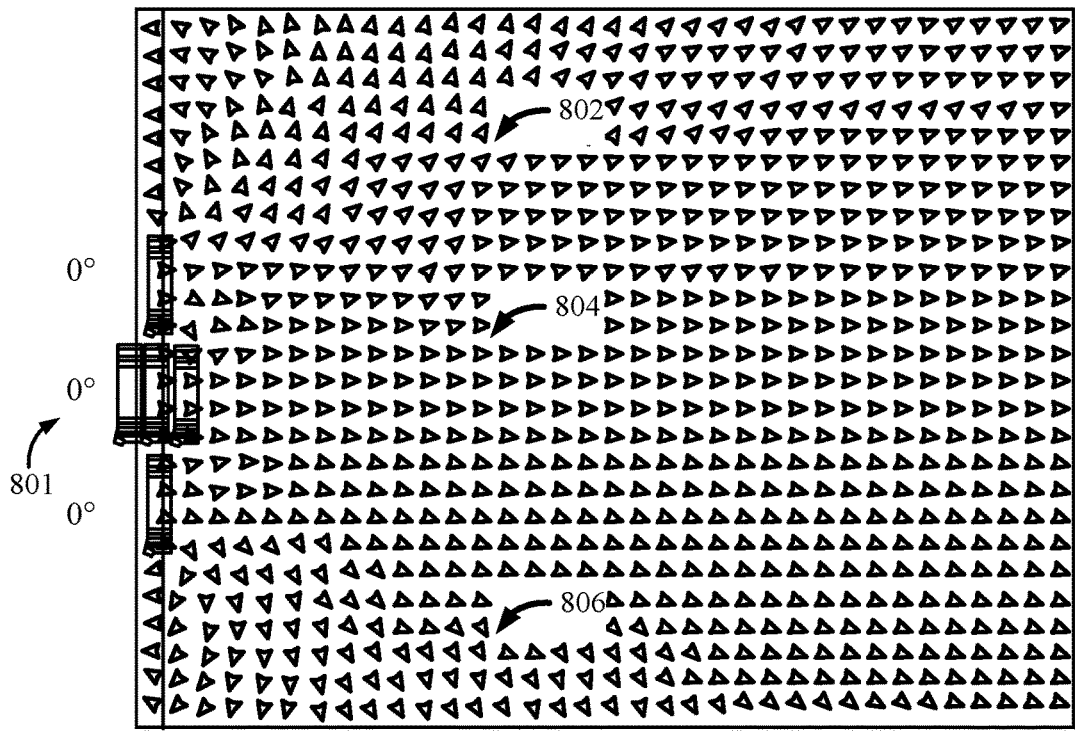
FIGS. 8A and 8B illustrate the H-field generated by coils, in accordance with certain aspects of the present disclosure.
Figure 8B:
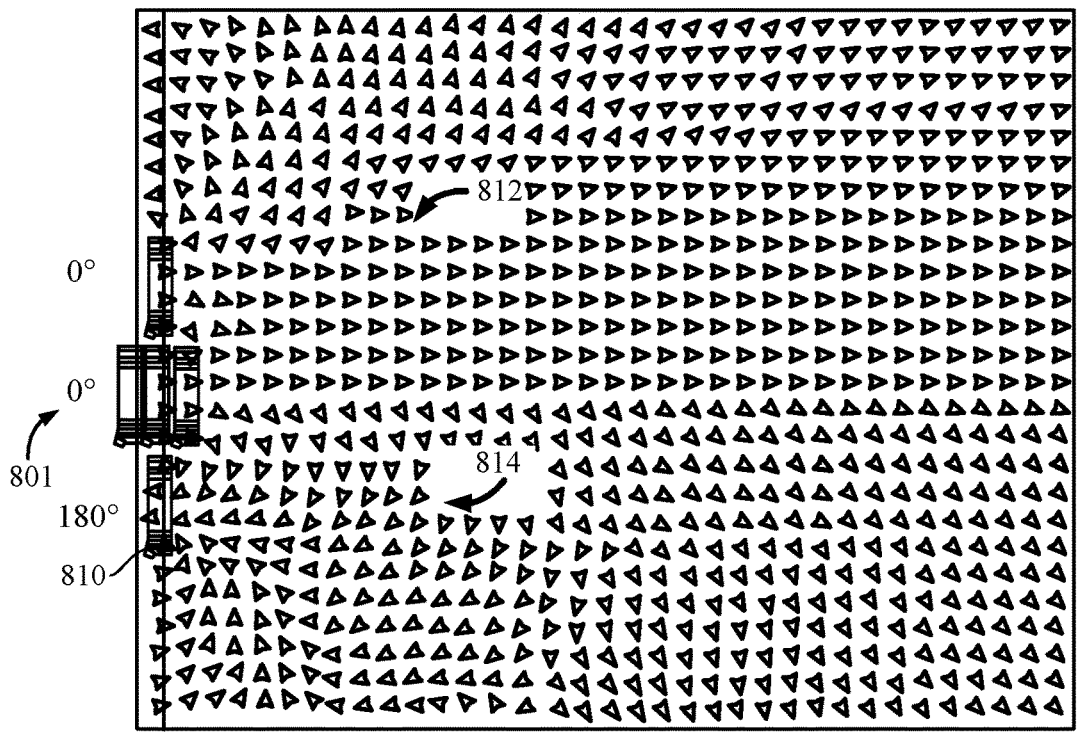

FIGS. 8A and 8B illustrate the H-field generated by coils 801, in accordance with certain aspects of the present disclosure. As illustrated in FIG. 8A, the H-field propagation is tilted at roughly positive and negative 45° angles at locations 802 and 806, and is roughly straight (i.e., angle of 0°) at location 804, when the five coils are driven with signals having the same phase. In certain aspects, one or more of the coils may be driven using a different phase (e.g., 180° out of phase) with respect to a signal used to drive another one of the coils 801. For example, as depicted in FIG. 8B, the bottom coil 810 is driven with a signal that is 180° out of phase with the other coils, adjusting the flow of the H-field from the coils 801. For example, the H-field is straight at location 812 and tilted 90° at location 814.

By driving the coil 810 with a phase-shifted signal, the H-field has shifted and is flowing out of the upper coils and into the phase-shifted coil 810. By manipulating the direction of the magnetic field, the transmitter can more effectively provide charge to an implant whose orientation couples better to the H-field direction of FIG. 8B. In certain aspects, the controller 240 may adjust the phase of one or more of the coils 801 based on an indication of whether the receiver (e.g., the implantable device) is receiving sufficient charge. For example, the controller 240 may receive feedback from the receiver indicating whether the receiver is receiving sufficient charge and adjust the phase of one or more of the coils based on the indication.

Figure 9:
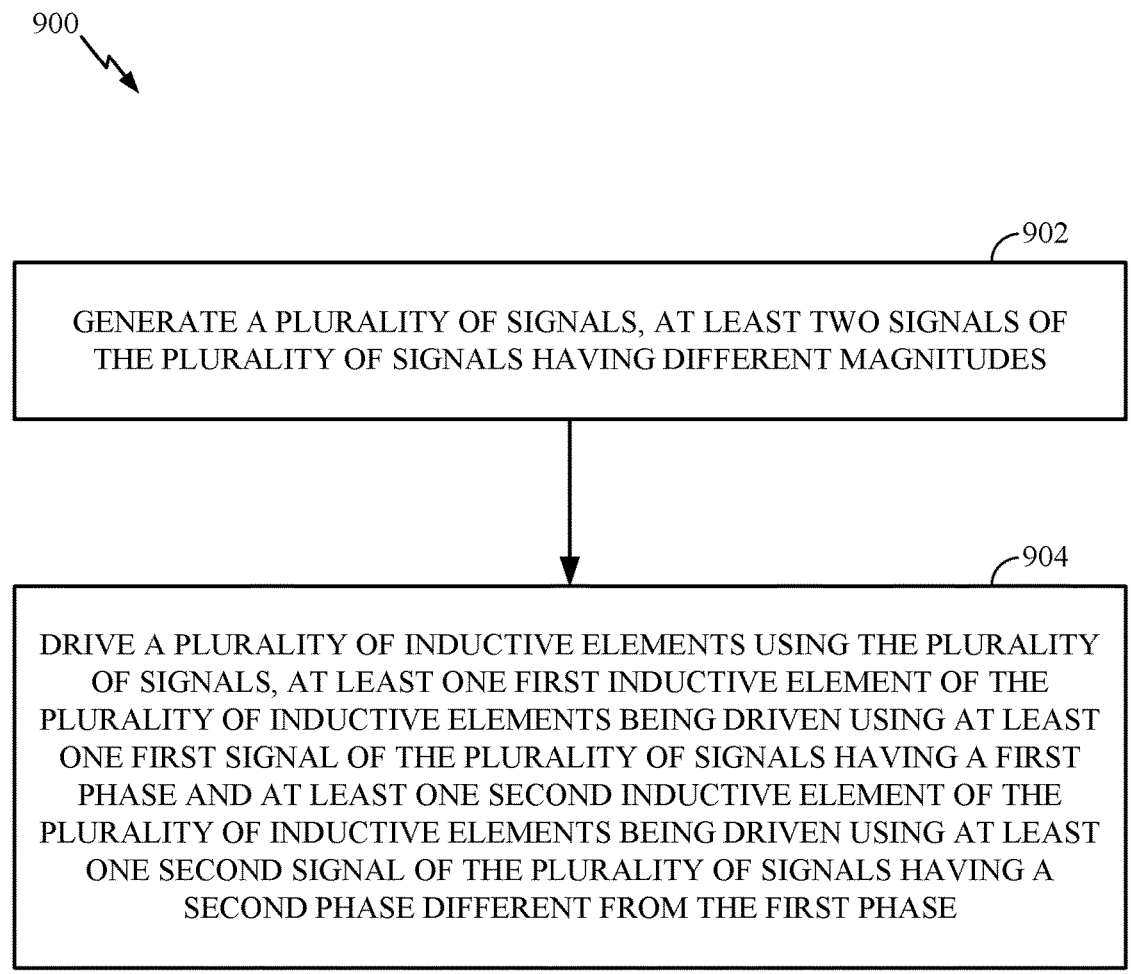
FIG. 9 is a flow diagram of example operations for wireless charging, in accordance with certain aspects of the present disclosure.

FIG. 9 is a flow diagram of example operations 900 for wireless charging, in accordance with certain aspects of the present disclosure. The operations 900 may be performed by an apparatus for wireless power transfer, such as a PTU, the transmitter 104 of FIG. 1, or the transmitter 204 of FIG. 2.

The operations 900 may begin, at block 902, with the apparatus generating a plurality of signals (e.g., current signals), where at least two signals of the plurality of signals have different magnitudes. The operations 900 continue, at block 904, with the apparatus driving a plurality of inductive elements (e.g., coils 402) using the plurality of signals. In certain aspects, at least one first inductive element of the plurality of inductive elements may be driven using at least one first signal of the plurality of signals having a first phase and at least one second inductive element of the plurality of inductive elements may be driven using at least one second signal of the plurality of signals having a second phase different from the first phase.

In certain aspects, at least one third inductive element of the plurality of inductive elements is located in a center portion of an arrangement of the plurality of inductive elements, and at least one fourth inductive element of the plurality of inductive elements is located at an outer portion of the arrangement. In this case, driving the plurality of inductive elements, at block 902, includes driving the at least one third inductive element using at least one signal of the plurality of signals having a different magnitude than at least one other signal of the plurality of signals used to drive the at least one fourth inductive element. In certain aspects, the at least one signal used to drive the third inductive element has a higher magnitude than the at least one other signal used to drive the fourth inductive element.

In certain aspects, the at least one first inductive element and the at least one second inductive element may be on different rows, on different columns, or both on different rows and different columns. In some cases, each of the inductive elements may be shaped as a polygon having four sides (e.g., a rectangle, a square, a trapezoid, a rhombus, etc.). In some cases, the inductive elements may be collectively positioned to form a square or rectangular arrangement (e.g., arrangement 400).

In certain aspects, the first inductive element and the second inductive element may be disposed on opposite sides of an arrangement of the plurality of inductive elements. In this case, the first signal may be 180 degrees out of phase from the second signal.

In certain aspects, the operations 900 also include the apparatus receiving an indication of whether a PRU (e.g., receiver 108 or receiver 208) is receiving sufficient charge and generating at least one control signal based on the indication, wherein the plurality of signals are generated based on the control signal, and wherein at least one phase of the plurality of signals is set by the control signal based on the indication. In certain aspects, the PRU comprises an implantable device, and the plurality of inductive elements may be configured to be arranged around a body to charge the implantable device.

Figure 10:
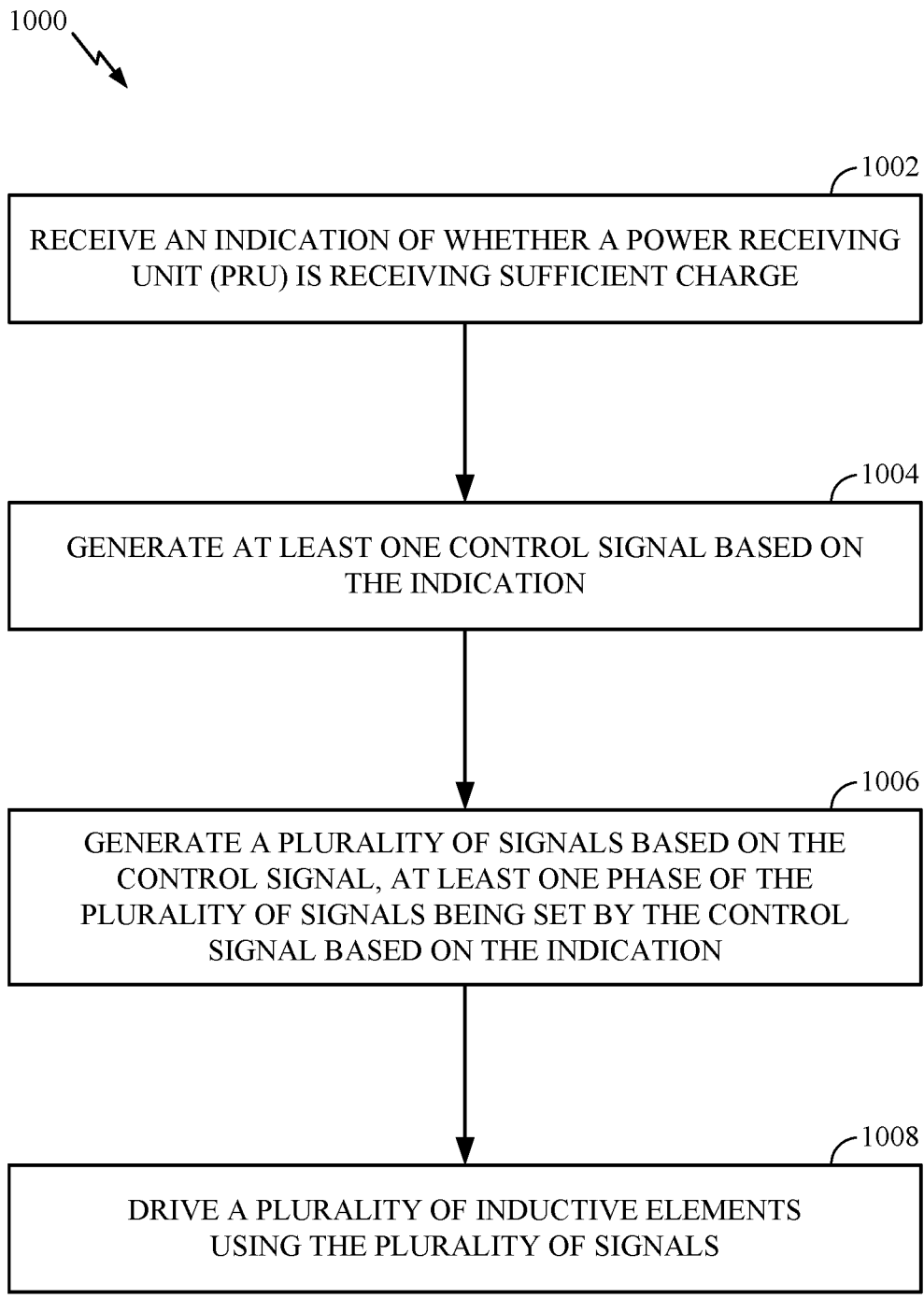
FIG. 10 is a flow diagram of example operations for wireless charging based on feedback from a receiver, in accordance with certain aspects of the present disclosure.

FIG. 10 is a flow diagram of example operations 1000 for wireless charging, in accordance with certain aspects of the present disclosure. The operations 1000 may be performed by an apparatus for wireless power transfer, such as a PTU, the transmitter 104 of FIG. 1, or the transmitter 204 of FIG. 2.

The operations 1000 may begin, at block 1002, with the apparatus receiving an indication of whether a PRU (e.g., receiver 108 or receiver 208) is receiving sufficient charge, and at block 1004, generating at least one control signal based on the indication. At block 1006, the apparatus generates a plurality of signals based on the control signal, where at least one phase of the plurality of signals is set by the control signal based on the indication. At block 1008, the apparatus uses the plurality of signals to drive a plurality of inductive elements (e.g., coils 402).

In certain aspects, at least one magnitude of the plurality of signals is set by the control signal based on the indication. In certain aspects, the operations 1000 also include the apparatus receiving another indication of whether the PRU is receiving sufficient charge after generating the control signal. In this case, the apparatus may generate another control signal to adjust the phase of one or more of the plurality of signals if the PRU is not receiving sufficient charge as determined based on the other indication.

The various operations of methods described above may be performed by any suitable means capable of performing the corresponding functions. The means may include various hardware and/or software component(s) and/or module(s), including, but not limited to a circuit, an application-specific integrated circuit (ASIC), or processor. Generally, where there are operations illustrated in figures, those operations may have corresponding counterpart means-plus-function components with similar numbering.

As used herein, the term "determining" encompasses a wide variety of actions. For example, "determining" may include calculating, computing, processing, deriving, investigating, looking up (e.g., looking up in a table, a database, or another data structure), ascertaining, and the like. Also, "determining" may include receiving (e.g., receiving information), accessing (e.g., accessing data in a memory), and the like. Also, "determining" may include resolving, selecting, choosing, establishing, and the like.

As used herein, a phrase referring to "at least one of" a list of items refers to any combination of those items, including single members. As an example, "at least one of: a, b, or c" is intended to cover: a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The various illustrative logical blocks, modules and circuits described in connection with the present disclosure may be implemented or performed with a general purpose processor, a digital signal processor (DSP), an ASIC, a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware, or any combination thereof. If implemented in hardware, an example hardware configuration may comprise a processing system. The processing system may be implemented with a bus architecture. The bus may include any number of interconnecting buses and bridges depending on the specific application of the processing system and the overall design constraints. The bus may link together various circuits including a processor, machine-readable media, and a bus interface. The bus interface may be used to connect a network adapter, among other things, to the processing system via the bus. The network adapter may be used to implement the signal processing functions of the physical (PHY) layer. In the case of a user terminal, a user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further.

The processing system may be configured as a general-purpose processing system with one or more microprocessors providing the processor functionality and external memory providing at least a portion of the machine-readable media, all linked together with other supporting circuitry through an external bus architecture. Alternatively, the processing system may be implemented with an ASIC with the processor, the bus interface, the user interface in the case of an access terminal), supporting circuitry, and at least a portion of the machine-readable media integrated into a single chip, or with one or more FPGAs, PLDs, controllers, state machines, gated logic, discrete hardware components, or any other suitable circuitry, or any combination of circuits that can perform the various functionality described throughout this disclosure. Those skilled in the art will recognize how best to implement the described functionality for the processing system depending on the particular application and the overall design constraints imposed on the overall system.

It is to be understood that the claims are not limited to the precise configuration and components illustrated above. Various modifications, changes and variations may be made in the arrangement, operation and details of the methods and apparatus described above without departing from the scope of the claims.

What is claimed is:

1. An apparatus for wireless charging, comprising:
a plurality of inductive elements; and
signal generation circuitry coupled to the plurality of inductive elements, the signal generation circuitry being configured to:
generate a plurality of signals, at least two signals of the plurality of signals having different magnitudes; and
drive the plurality of inductive elements using the plurality of signals, at least one first inductive element of the plurality of inductive elements being driven using at least one first signal of the plurality of signals having a first phase and at least one second inductive element of the plurality of inductive elements being driven using at least one second signal of the plurality of signals having a second phase different from the first phase, wherein:
at least one third inductive element of the plurality of inductive elements is located in a center portion of an arrangement of the plurality of inductive elements;
at least one fourth inductive element of the plurality of inductive elements is located at an outer portion of the arrangement; and
the at least one third inductive element is driven using at least one third signal of the plurality of signals having a different magnitude than at least one fourth signal of the plurality of signals used to drive the at least one fourth inductive element.

2. The apparatus of claim 1, wherein the at least one third signal used to drive the third inductive element has a higher magnitude than the at least one fourth signal used to drive the fourth inductive element.

3. The apparatus of claim 1, wherein:
the at least one first inductive element and the at least one second inductive element are on different rows, on different columns, or both on different rows and different columns.

4. The apparatus of claim 1, wherein each of the inductive elements is shaped as a polygon having four sides.

5. The apparatus of claim 4, wherein the inductive elements are positioned to form a square or rectangular arrangement.

6. The apparatus of claim 1, wherein:
the first inductive element and the second inductive element are disposed on opposite sides of the arrangement of the plurality of inductive elements; and
the first signal is 180 degrees out of phase from the second signal.

7. The apparatus of claim 1, further comprising a controller configured to receive an indication of whether a power receiving unit (PRU) is receiving sufficient charge and generate at least one control signal based on the indication, wherein the signal generation circuitry is configured to generate the plurality of signals based on the control signal, and wherein at least one phase of the plurality of signals is set by the control signal based on the indication.

8. The apparatus of claim 7, wherein the PRU comprises an implantable device, and wherein the plurality of inductive elements are configured to be arranged around a body to charge the implantable device.

9. The apparatus of claim 1, wherein a phase of each of the plurality of signals is selected based on a location of a respective inductive element driven by the signal.

10. An apparatus for wireless charging, comprising:
a plurality of inductive elements, wherein at least one first inductive element of the plurality of inductive elements is located at a center portion of an arrangement of the plurality of inductive elements, and wherein at least one second inductive element of the plurality of inductive elements is located at an outer portion of the arrangement;
a controller configured to receive an indication of whether a power receiving unit (PRU) is receiving sufficient charge and generate at least one control signal based on the indication; and
signal generation circuitry coupled to the plurality of inductive elements and configured to:
generate a plurality of signals based on the control signal, at least one phase of the plurality of signals being set by the control signal based on the indication; and
drive the plurality of inductive elements using the plurality of signals, wherein the signal generation circuitry is configured to generate the plurality of signals by generating at least one first signal to drive the at least one first inductive element and at least one second signal to drive the second inductive element, the first signal having a higher magnitude than the second signal.

11. The apparatus of claim 10, wherein the indication is received from the PRU.

12. The apparatus of claim 10, wherein at least one magnitude of the plurality of signals is set by the control signal based on the indication.

13. The apparatus of claim 10, wherein the controller is configured to:
receive another indication of whether the PRU is receiving sufficient charge after generating the control signal; and
generate another control signal to adjust the phase of one or more of the plurality of signals if the PRU is not receiving sufficient charge as determined based on the other indication.

14. The apparatus of claim 10, wherein two or more of the plurality of signals have different phases.

15. The apparatus of claim 10, wherein a third signal of the plurality of signals is 180 degrees out of phase from a fourth signal of the plurality of signals.

16. The apparatus of claim 10, wherein the PRU comprises an implantable device, and wherein the plurality of inductive elements are configured to be arranged around a body to charge the implantable device.

17. A method for wireless charging, comprising:
generating a plurality of signals via signal generation circuitry, at least two signals of the plurality of signals having different magnitudes; and
driving a plurality of inductive elements using the plurality of signals generated via the signal generation circuitry, the plurality of inductive elements being coupled to the signal generation circuitry, at least one first inductive element of the plurality of inductive elements being driven using at least one first signal of the plurality of signals having a first phase, and at least one second inductive element of the plurality of inductive elements being driven using at least one second signal of the plurality of signals having a second phase different from the first phase, wherein:
at least one third inductive element of the plurality of inductive elements is located in a center portion of an arrangement of the plurality of inductive elements;
at least one fourth inductive element of the plurality of inductive elements is located at an outer portion of the arrangement; and
driving the plurality of inductive elements comprises driving the at least one third inductive element using at least one third signal of the plurality of signals having a different magnitude than at least one fourth signal of the plurality of signals used to drive the at least one fourth inductive element.

18. The method of claim 17, wherein the at least one third signal used to drive the third inductive element has a higher magnitude than the at least one fourth signal used to drive the fourth inductive element.

19. The method of claim 17, wherein:
the at least one first inductive element and the at least one second inductive element are on different rows, on different columns, or both on different rows and different columns.

20. The method of claim 17, wherein each of the inductive elements is shaped as a polygon having four sides.

21. The method of claim 20, wherein the inductive elements are positioned to form a square or rectangular arrangement.

22. The method of claim 17, wherein:
the first inductive element and the second inductive element are disposed on opposite sides of the arrangement of the plurality of inductive elements; and
the first signal is 180 degrees out of phase from the second signal.

23. The method of claim 17, further comprising:
receiving an indication of whether a power receiving unit (PRU) is receiving sufficient charge; and
generating at least one control signal based on the indication, wherein the plurality of signals are generated based on the control signal, and wherein at least one phase of the plurality of signals is set by the control signal based on the indication.

24. The method of claim 23, wherein the PRU comprises an implantable device, and wherein the plurality of inductive elements are configured to be arranged around a body to charge the implantable device.

25. A method for wireless charging, comprising:
receiving an indication of whether a power receiving unit (PRU) is receiving sufficient charge;
generating at least one control signal based on the indication;
generating a plurality of signals based on the control signal via signal generation circuitry, at least one phase of the plurality of signals being set by the control signal based on the indication; and
driving a plurality of inductive elements using the plurality of signals, the plurality of inductive elements being coupled to the signal generation circuitry, wherein:
at least one first inductive element of the plurality of inductive elements is located at a center portion of an arrangement of the plurality of inductive elements;
at least one second inductive element of the plurality of inductive elements is located at an outer portion of the arrangement; and
the generating of the plurality of signals comprises generating at least one first signal to drive the at least one first inductive element and generating at least one second signal to drive the at least one second inductive element, the first signal having a higher magnitude than the second signal.

26. The method of claim 25, wherein at least one magnitude of the plurality of signals is set by the control signal based on the indication.

27. The method of claim 25, further comprising:
receiving another indication of whether the PRU is receiving sufficient charge after generating the control signal; and
generating another control signal to adjust the phase of one or more of the plurality of signals if the PRU is not receiving sufficient charge as determined based on the other indication.

* * * * *